United States Patent [19]
Giaever

[11] 3,970,518
[45] July 20, 1976

[54] MAGNETIC SEPARATION OF BIOLOGICAL PARTICLES

[75] Inventor: Ivar Giaever, Schenectady, N.Y.

[73] Assignee: General Electric Company, Schenectady, N.Y.

[22] Filed: July 1, 1975

[21] Appl. No.: 592,195

[52] U.S. Cl. .............................. 195/1.5; 23/230 B; 195/103.5 R; 210/222; 209/8; 424/12
[51] Int. Cl.² .................. G01N 27/00; G01N 33/16
[58] Field of Search ..................... 23/230 B; 424/12; 210/222; 195/1.5, 103.5 R; 209/8

[56] References Cited
UNITED STATES PATENTS

| | | | |
|---|---|---|---|
| 3,470,067 | 9/1969 | Warren | 210/222 X |
| 3,539,509 | 11/1970 | Heitmann | 210/222 X |
| 3,657,119 | 4/1972 | Turbeville | 210/222 X |
| 3,843,324 | 10/1974 | Edelman | 424/12 X |

Primary Examiner—Morris O. Wolk
Assistant Examiner—Sidney Marantz
Attorney, Agent, or Firm—Leo I. MaLossi; Joseph T. Cohen; Jerome C. Squillaro

[57] ABSTRACT

Small magnetic particles coated with an antibody layer are used to provide large and widely-distributed surface area for sorting out and separating select viruses, bacteria and other cells from multi-cell, bacteria or virus populations.

8 Claims, 2 Drawing Figures

MAGNETIC SEPARATION OF BIOLOGICAL PARTICLES

BACKGROUND OF THE INVENTION

This invention relates to the detection of biological particles by the utilization of the phenomenon by which such biological particles interact specifically either immunologically or non-immunologically.

Construction of diagnostic devices for use in the immunological detection of proteins as well as methods and apparatus for the purification of proteins are disclosed in the related copending U.S. Applications of Giaever, Ser. No. 266,278, filed June 26, 1972 (now abandoned) and Ser. No. 384,113, filed July 30, 1973 (now abandoned). Other constructions of diagnostic devices for use in the immunological detection of biological particles are disclosed in the related copending U.S. Applications of Giaever, Ser. No. 445,204, filed Feb. 25, 1974 and Ser. No. 580,603, filed May 27, 1975. An improved diagnostic method for determining the presence or absence of select biological particles by the utilizaton of "tagging" (e.g. radioactive isotopes) and a cleaving operation is disclosed in copending U.S. Patent Application Ser. No. 573,610 - Giaever, filed May 1, 1975.

Method and apparatus specific for the detection of viruses, bacteria and other cells is disclosed in U.S. Pat. No. 3,853,467 - Giaever.

This application is related to concurrently filed U.S. Pat. Application Ser. No. 592,196 - Giaever entitled "Magnetic Reduction in Period of Diffusion for Immunological Reaction" commonly assigned and filed July 1, 1975.

DESCRIPTION OF THE INVENTION

The method according to this invention for sorting out and separating a select cell population from a mixed cell population comprises the steps of applying to the surface of small magnetic particles a coating of an antibody to the select cell, bacteria or virus population: moving these antibody-coated magnetic particles through a liquid containing the mixed population whereby the members of the cell, bacteria or virus population become affixed to the antibody coatings on the particles, separating the coated magnetic particles with such members attached thereto from the rest of the mixed population; introducing the coated magnetic particles and attached members into a solution of cleaving agent whereby the bonds between the antibody and the members of the select population is broken and separating the antibody-coated magnetic particles and solution containing the select population of cells, bacteria or viruses from each other.

BRIEF DESCRIPTION OF THE DRAWING

The subject matter of the instant invention for which protection is sought is presented as claims at the conclusion of the written description of the invention set forth herein. The description sets forth the manner and process of making and using the invention and the accompanying drawing forms part of the description schematically illustrating one embodiment. The views include:

MANNER AND PROCESS OF MAKING AND USING THE INVENTION

Figure 1:
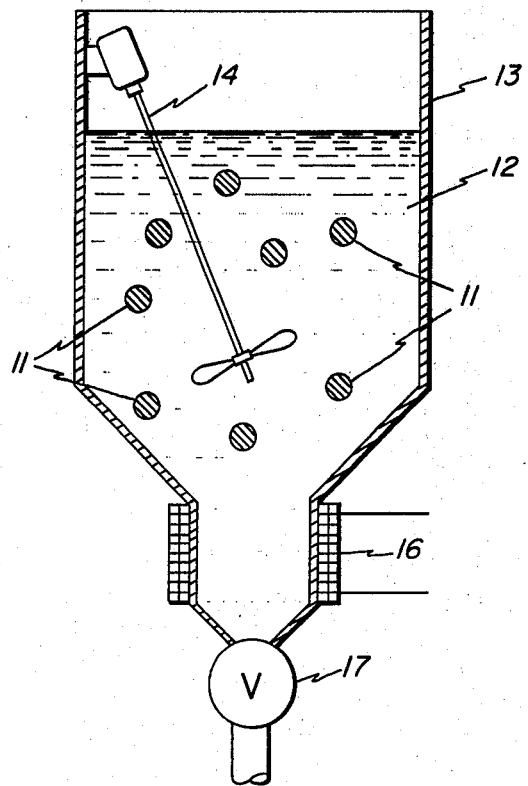
FIG. 1 showing a section through apparatus that may be employed for the distribution of small magnetic particles in a liquid and subsequent separation of the particles from the liquid.

Referring now to the drawing, having identified the particular (select) cell population (or population of virus or bacteria) that is to be separated from a mixed population, small magnetic particles or spheres 11 are first provided with a monomolecular coating of antibody to this select population. This may be accomplished by dispersing clean (uncoated) magnetic particles 11 in a liquid 12 containing a large concentration of these antibodies. This dispersion or distribution may be easily accomplished in reaction vessel 13 by the use of agitating means 14.

Depending upon the concentration of the antibodies in liquid 12, a monomolecular layer of the antibodies attaches itself to the surfaces of the clean magnetic particles. A contact period of less than one hour is usually sufficient with antibody concentrations of 10 micrograms/ml.

Ferromagnetic, ferrimagnetic and superparamagnetic are useful in the practice of this invention. Other suitable magnetic materials include oxides, such as, for example, ferrites, perovskites, chromites and magnetoplumbites. The particles can range in size from colloidal to about 10 microns.

Separation of the resulting antibody-coated magnetic spheres 11 from liquid 12 is readily accomplished by actuating coil 16 and opening valve 17. As the metallic particles 11 enter the field created by coil 16, they are captured and immobilized while liquid 12 is unaffected and leaves vessel 13.

Next, valve 17 is closed, coil 16 is deactivated permitting free flow of the coated magnetic particles 11 and the solution containing the mixed population is introduced in place of the previous liquid in reaction vessel 13. Agitating means 14 quickly and effectively distributes the antibody-coated magnetic particles 11 through the mixed population facilitating the attachment of the members of the select population to the antibody-coated surfaces forming a complex therewith. The period of agitation may vary from less than hour to as much as a 24-hour period depending upon the concentration of the select population present; the lower the concentration, the longer the period of exposure required.

Figure 2:
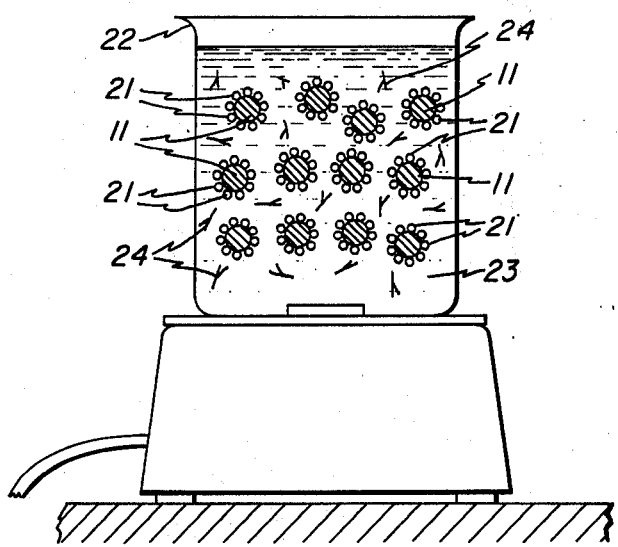
FIG. 2 shows in elevation and partially in section apparatus for contacting the coated magnetic particles with cleaving agent solution.

Having attached the select population to the surfaces of magnetic particles 11, these coated particles and attachments are separated from the liquid containing the mixed population in the same manner as described hereinabove in connection with the first separation. Thereafter, the coated magnetic particles 11 (shown in FIG. 2 covered with antibodies 21) with the members of the select population affixed thereto are washed and transferred to a container 22 containing cleaving agent solution 23. If desired, the washing can be accomplished while the particles 11 are held captive by the coil 16. A 0.1 normal (N) citric acid solution is preferred as solution 23 for the purposes herein described. The range of concentrations of the citric acid that may be used for obtaining the desired results are approximately 0.01 to 1.0 N.

The cleaving agent must be sufficiently strong to break the bond between the members of the select population and the antibody layer to which they are complexed, but not strong enough to cleave, or otherwise affect, the bond between the first (specific) monomolecular layer of antibodies 21 and the solid surface of any given magnetic particle 11 to which the layer is adsorbed. Other suitable weak acids that may be utilized are 0.1 N malic acid and 0.1 N formic acid. Stronger acids such as hydrochloric acid and sulfuric acid may also be utilized but in a much smaller concentration (i.e. approximately 0.01 N). In the case of an acid cleaving agent preferably the pH is the range between 2 and 5, although a pH as low as 1.0 has been satisfactorily utilized with 0.1 N hydrochloric acid.

With respect to alkaline and high salt concentration solutions useful as cleaving agents, the alkaline solution useful herein would have a pH in the range 9–13, and typically, a 0.2 N sodium hydroxide solution has been used. Various salt solutions of elevated salt concentration, such as NaCl and NaI are known to function as cleaving agents.

Facilitation of the stripping of the select population members 24 (cells, bacteria, viruses) from particles 11 coated with antibodies 21 may be facilitated by using a conventional magnetic stirrer 26 actuated by magnetic device 27. Having separated the members 24 of the select population from the magnetic particles 11, which retain the monomolecular coating of antibodies 21, it is then merely necessary to separate magnetic particles 11 from solution 23. This may be readily accomplished by emptying the contents of container 22 into reaction vessel 13, activating coils 16, opening valves 17 and collecting the discharge from vessel 13. This liquid discharge will contain therein the select population members 24 segregated from the balance of the mixed population.

Preferably magnetic particles 11 already coated with specific antibodies would be made available commercially for carrying on the separation of a select population according to this invention.

What I claim as new and desire to secure by Letters Patent of the United States is:

1. A method for the separation of a select population of cells, bacteria or viruses from a mixed population comprising the steps of:
   contacting a solution of said mixed population containing members of said select population with a plurality of small magnetic particles each of which is coated with a layer of antibodies to the select population bonded thereto,
   magnetically separating said magnetic particles from said solution, said magnetic particles having on surface area thereof members of said select population affixed as a complex to said layer of antibodies,
   contacting these coated magnetic particles with said members affixed thereto with a cleaving agent solution to detach said members of the select populaton from said antibody-coated magnetic particles and
   magnetically separating the antibody-coated magnetic particles from the cleaving agent solution now containing said members of the select population.

2. The separation method recited in claim 1 wherein the magnetic particles are selected from the group consisting of ferromagnetic and ferrimagnetic materials.

3. The separation method recited in claim 1 wherein after separation thereof from the solution the magnetic particles are held by means of an electrically induced magnetic field and washed.

4. The separation method recited in claim 1 wherein the cleaving agent is a weak acid solution.

5. The separation method recited in claim 4 wherein the acid is citric acid.

6. The separation method recited in claim 1 wherein the select populatin is of cells.

7. The separation method recited in claim 1 wherein the select population is bacterial.

8. The separation method recited in claim 1 wherein the select population is viral.

* * * * *